United States Patent [19]

Kreb, III

[11] 4,175,559

[45] Nov. 27, 1979

[54] SEALABLE SYRINGE

[76] Inventor: Robert J. Kreb, III, Rolling Hill Rd., Skillman, N.J. 08558

[21] Appl. No.: 893,922

[22] Filed: Apr. 6, 1978

[51] Int. Cl.$^2$ ............................................. A61M 5/00
[52] U.S. Cl. ................................. 128/218 R; 128/234
[58] Field of Search ................... 128/218 R, 215, 216, 128/234, 2 F, 224

[56] References Cited

U.S. PATENT DOCUMENTS

| | | | |
|---|---|---|---|
| 1,531,213 | 3/1925 | Nimmer | 128/224 |
| 1,841,406 | 1/1932 | Galazin | 128/251 |
| 1,853,202 | 4/1932 | Catlin | 128/239 X |
| 2,134,291 | 10/1938 | Schultz | 128/237 |
| 2,355,012 | 8/1944 | Reifsnyder | 128/231 |
| 2,369,304 | 2/1945 | Lewis | 128/215 |
| 2,866,580 | 12/1958 | Nissen | 222/512 |
| 3,143,109 | 8/1964 | Gewertz | 128/2 F |
| 3,234,945 | 2/1966 | Waldman et al. | 128/227 |
| 3,640,431 | 2/1972 | Plumer | 222/48 |
| 3,747,812 | 7/1973 | Karman et al. | 128/215 X |
| 3,848,581 | 11/1974 | Cinqualbre et al. | 128/2 F |
| 3,872,864 | 3/1975 | Allen | 128/218 M |
| 4,043,336 | 8/1977 | Kreb | 128/218 R |

*Primary Examiner*—John D. Yasko
*Attorney, Agent, or Firm*—Albert Sperry; Frederick A. Zoda; John J. Kane

[57] ABSTRACT

A sterile syringe including a cylindrical housing and a plunger positioned therein movable axially, the housing including a headwall defining a headwall aperture therein which is selectively registrable with a mated aperture defined by a cap member which extends over the head of the syringe, the cap member is mounted upon a stem in the center thereof which secures it to the center of the housing of the syringe, the stem allows relative rotation between the cap member and the syringe housing to selectively align and misalign the aperture in the cap with respect to the aperture in the housing, the end of the cap and the headwall of the housing being slightly spaced from one another to define an insulating space therebetween in which is positioned a sealing member such as a rubber grommet which seals the chamber within the syringe housing whenever the aperture in the headwall of the housing is not aligned with the aperture in the cap due to the cap being rotated slightly with respect to the housing, the aperture in the cap communicating to a nipple which is adapted to receive the needle secured thereto such that movement of the cap by rotation between an opened and a closed position selectively allows or prevents fluid flow communication between the sterile internal chamber and the needle, also possibly including a tab means movable between two protrusions which position the cap member in an opened or closed orientation.

10 Claims, 5 Drawing Figures

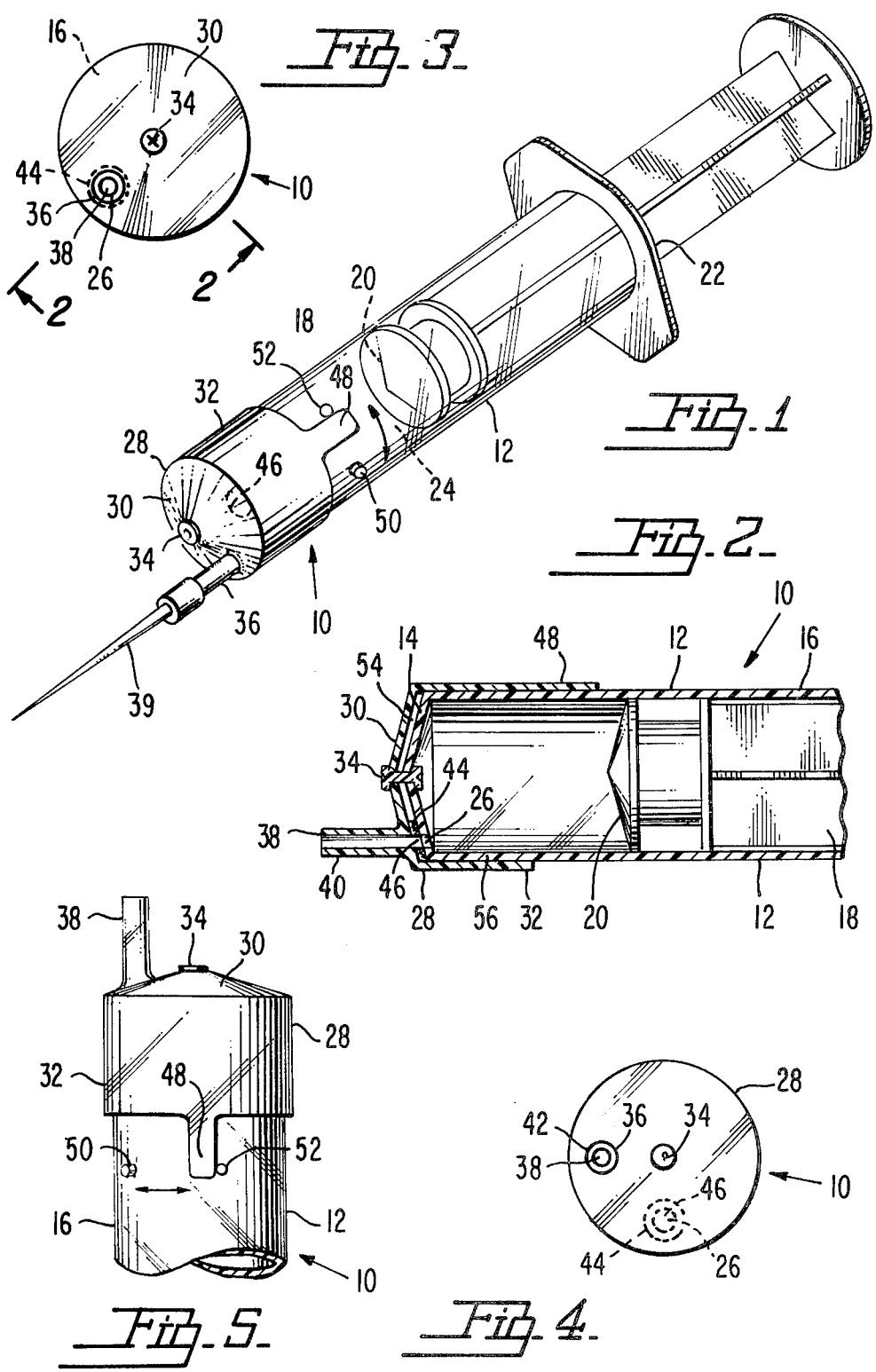

SEALABLE SYRINGE

BACKGROUND OF THE INVENTION

1. Field of the Invention

The present invention deals with the field of syringe devices usable with hypodermic needle constructions. It is often convenient to construct such devices such that the portion of the hypodermic needle which penetrates the skin of the patent is disposable whereas the remainder of the syringe body is reusable. Basically, a hypodermic syringe is usable for the injection of fluids at selective locations with the soft tissues of the human body. However, it is often desirable to withdraw fluids, most usually blood or urine from the human body for various reasons.

When fluids are withdrawn by persons by the use of a hypodermic syringe, it is desirable to prevent any secondary contamination of the fluids, so withdrawn, subsequent to entering syringe body. In this respect, it is desirable to provide a means for minimizing contact between the atmosphere or any other contaminating agent and a fluid which has recently been withdrawn. In hospitals to seal a syringe, laboratory technicians, nurses and physicians often resort to bending the needle at the end of a syringe to minimize contact between the atmosphere and the withdrawn fluid. Such a procedure is initially dangerous to the technician or nurse and also does not provide an effective hermetic seal. Another attempt to maintain the withdrawn fluid in a sterile condition is to insert the needle immediately into a cork or similar device. These primitive methods have been utilized to prevent secondary contamination of withdrawn blood and the like since previously designed constructions for providing a sterile syringe have been either too costly or proved to be inefficient in operation. It would be desirable to have an effective device such as shown under the present invention which would enable the fluid within the hypodermic syringe to be sealed while the hypodermic needle is still located within the body of the patent. In this manner, secondary contamination of the reservoir within the housing of the syringe device is minimized.

2. Description of the Prior Art

Many patents have been granted on syringe devices which are usable with hypodermic needles for sealing the internal environment of the syringe device with respect to the external ambient atmosphere. One such U.S. Pat. is No. 3,872,864 issued Mar. 25, 1975 to Allen in which a plurality of internal sealable chambers is provided for use with a double syringe assembly for prefilled plastic syringes which are completely disposable. This design and those similar thereto include complicated sealing arrangements and isolating devices. Most of these designs are usable for maintaining a fluid within the syringe in an uncontaminated condition prior to insertion in the soft tissue of the human body. The present invention has a primary useful function in the field of syringes used for the withdrawing of fluids from the human body.

When fluids are withdrawn from the human body, the main problem is to place the withdrawn fluid within a culture medium for isolation of bacterial or viral contaminants. The difficulty arises when secondary contamination occurs during the transference from the syringe device to the location of the culture medium. During this critical time period, a secondary contamination could occur which would erroneously suggest the presence of a bacterial or viral entity within the blood of the subject which has entered the culture medium only by way of the secondary contamination and not as a result of being located within the body of the subject. The present invention includes a design for eliminating such secondary contaminations.

U.S. Pat. No. 4,043,336 in the name of the present inventor also provides a system for selectively valving the end of the syringe. That system utilizes additional moveable members and additional sealing means other than the simple rubber grommet of the present invention and as such is a different configuration. Also that invention requires the gripping of the needle member itself for rotation of the respective apertures to cause or prevent flow and does not have the ease of grasping and movement as in the present invention wherein an external collar is provided for movement between the open and sealed position.

SUMMARY OF THE INVENTION

The present invention provides a sealable syringe device by mounting a rotatably movable cap member over the head area of a conventional syringe housing. The syringe housing includes a head area and a generally cylindrical sidewall area and an open end which is adapted to receive therethrough a plunger for controlling the movement of fluid into and out of the sterile chamber. The sterile chamber itself is defined by the sidewalls of the syringe, the headwall of the syringe, and the plunger head. By movement of the plunger means into and out of the syringe housing the volume of space within the sterile chamber is controlled and the movement of fluids into and out of the chamber is controlled.

The housing of the present invention does not utilize any needle mounting location since the needle itself will be mounted to the cap member. The headwall of the housing includes a headwall aperture therein and a centrally located stem. The cap member is mounted to the stem to allow relative rotational movement between the cap and housing. The cap member has a nipple thereon which includes an attachment means such that any conventional needle may be secured to the nipple means. The nipple means includes a nipple aperture centrally located therein which can be alignable with the housing aperture.

By rotation of the cap member with respect to the housing the operator can cause alignment or misalignment between the nipple aperture and the housing aperture and thereby allow or prevent fluid flow through the needle.

The rotational movement between the cap and the housing is achieved by the stem which extends axially with respect to both members. In this manner rotation of the cap in one direction will cause alignment of the housing aperture and the cap aperture and thereby allow fluid flow communication between the sterile chamber and the needle. At the other position the needle will be prevented from fluid flow communication with the sterile environment. To assure the maintaining of the sterile condition of the sterile chamber a sealing means such as a rubber grommet or the like may be positioned peripherally about the joining interface of the nipple aperture and housing aperture. To facilitate placement of this grommet it is desirable to maintain the headwall and the head portion of the cap member disposed in a slightly spaced relation with respect to one another to thereby create an insulating air space therebetween. In this insulating air space is located the sealing grommet peripherally around the edge along which the selectively alignable apertures meet. Therefore when in the misaligned orientation the under surface of the head portion of the cap will seal the top of the rubber grommet and provide an effective seal with respect to the sterile chamber.

Alternatively however the rubber grommet could be secured to the bottom of the cap and as such rotation of the cap will cause rotation of the sealing means. In this manner the chamber will still remain sealed and will only provide some element of communication into the insulating space which itself is sealed from the external environment by the sealing caused by close abutment of the side portions of the cap member with the sidewalls of the syringe housing.

Another alternative structure includes a tab means which extends downwardly from the cap member and is movable between two protrusions one of which indicates the opened position and one of which indicates the closed position. These protrusions would be slight bumps on the outside cylindrical wall of the housing and would provide a convenient set of stopping means for easily indicating to the operator the opened and closed positions.

It is an object of the present invention to provide a sealable syringe device for withdrawing fluids from the human body.

It is an object of the present invention to provide a sealable syringe device which is usable with disposable hypodermic needles.

It is an object of the present invention to provide a simple and inexpensive construction which eliminates contaminations of fluids when withdrawn from the body.

It is an object of the present invention to provide a hypodermic syringe which can also be used for insertion of fluids into the human body.

It is an object of the present invention to provide a sealable hypodermic syringe which is particularly of use for withdrawing fluids from the body rather than insertion of fluids into the body.

It is an object of the present invention to provide a safe means for preventing secondary contamination of fluids withdrawn from the body.

It is an object of the present invention to provide a syringe which is easibly moved from a closed valve position to an open valve position.

It is an object of the present invention to provide a syringe which includes a valve in the head area which is easy to grip and move from an opened to a closed position and back.

It is an object of the present invention to provide a syringe having a valve in the head thereof including an externally rotatable member for facilitate use thereof.

It is an object of the present invention to provide a sealable syringe including an insulating cushion of air positioned between an outer rotatable member and the headwall of the syringe body.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a perspective view showing a preferred embodiment of the syringe of the present invention;

FIG. 2 is a cross-sectional view through FIG. 1 along lines 2,2.

FIG. 3 is an end view of an embodiment of the present invention showing the cap member in the opened position;

FIG. 4 is an end view of an embodiment of the present invention showing the cap member in the closed position; and FIG. 5 is a side view of an embodiment of the tab member of the present invention shown in the closed position.

DETAILED DESCRIPTION OF THE PREFERRED EMBODIMENT

The present invention provides a syringe 10 which is sealable by rotation of a cap member 28 which fits around the discharge end of the syringe. The syringe generally comprises a housing 12 having a headwall 14 and a generally cylindrical sidewall 16.

A plunger means 18 is located within the housing 12 and is movable axially therein to control the inflow and outflow of fluids from the sterile chamber 24 which is defined within the housing. In particular the sterile chamber 24 is defined by the sidewalls 16 and the headwall 14 of the housing and the head 20 of the plunger 18. The plunger 18 extends inwardly into the housing through the open end 22 thereof and in this manner it defines the sterile limits of the chamber 24.

Fluid is introduced and expelled with respect to the chamber 24 through the housing aperture 26 which is located in the head wall 14. Also the head wall 14 defines the mounting location for the stem member 34. The stem member 34 provides the means for mounting the cap member 28 with respect to the housing 12. The housing 12 and the cap member 28 are able to be rotatable with respect to one another due to the central axial location of the stem member 34. The stem member can be loosely fitted within the cap member 28 as well as it may be loosely fitted within the head wall 14 or it may be fixedly mounted in either but not both of these members.

The cap member 28 generally comprises a head portion 30 and a side portion 32. The side portion snugly abuts the outside walls of the side walls 16 of the housing 12. The close fitting of these two parts creates a capped sealing surface 56 entirely about the periphery of the generally cylindrical housing 12 in order to seal the insulating space 54 from the external environment. The insulating space 54 is defined by the positioning of the head portion 30 of the cap member 28 disposed in a spaced relationship with respect to the headwall 14 of the housing 12. In this manner an insulating space is defined therebetween in which may be located the sealing means 42.

Sealing means 42 provides the means for allowing or preventing fluid flow communication between the sterile chamber 24 in the external environment. To communicate fluid therebetween a nipple means 36 is included in the external surface of the cap member 28. Nipple means 36 provides the mounting location for a needle 39. The needle 39 may be secured to the nipple means 36 through an attachment means 40 or other similar securement means. In FIG. 2 the attachment means is shown as a threaded section however this could be a bayonet mount or other similar standard needle mounting configurations.

The needle includes a centrally located needle aperture 38 which provides the means for fluid flow communication from the sterile chamber 24 to the needle 39.

The sealing means 42 preferably takes the form of a rubber grommet 44 which is peripherally located about the interface between the nipple aperture 38 and the housing aperture 26. The rubber grommet 44 thereby defines its own grommet aperture 46 therein.

To further aid in accurately and conveniently causing registration or non-registration between the housing aperture 26 and the nipple aperture 38 a tab means 48 may be included extending downwardly from the cap member 28. This tab means 48 is adapted to abut two protrusions located extending outwardly from the sidwalls 16 of the housing 12. These protrusions are labeled the opened protrusion 50 and the closed protrusion 52. These protrusions are chosen at locations on the sidewall 16 such that when the tab means is in engagement with the opened protrusion 50 the nipple aperture 38 and the housing aperture 26 will be in perfect registration. Alternatively when the tab means 48 is in abutment with the protrusion 52 which indicates a closed condition the apertures 38 and 26 will not be aligned and therefore the internal chamber 24 will be sealed with respect to the external environment by the rubber grommet 44 or sealing means 42.

In operation with the rubber grommet preferably fixedly cemented or other wise secured to the headwall, the rotation of the cap member will cause the apertures 26 and 38 to be misaligned and as such the sterile chamber 24 will be sealed by the under surface of the head portion 30 of the cap member 28 which will seal off the top of the sealing means 42. In this alternative configuration if the rubber grommet 44 is secured to the bottom of the cap member 28 then the flow through the housing aperture 26 will be limited only to flow into the insulation space 54 therebetween and as such will be sealed by the cap sealing surface 56 extending peripherally around the outer wall of the sidewall 16 underneath the closely fitting side portions 32 of the cap member 28. In this manner fixed sealing will be created with either configuration.

While particular embodiments of this invention have been shown in the drawings and described above, it will be apparent that many changes may be made in the form, arrangement and positioning of the various elements of the combination. In consideration thereof it should be understood that preferred embodiments of this invention disclosed herein are intended to be illustrative only and not intended to limit the scope of the invention.

I claim:

1. A sealable syringe comprising:
   (a) a housing defining a chamber therein which is sterile, said housing including a headwall, a sidewall and an open end, said headwall defining a housing aperture therein and a stem member mounted extending axially outward therefrom;
   (b) a plunger located within said chamber and being movable axially with respect to said housing to vary the total volume of said chamber;
   (c) a cap member including a head portion and a side portion located about said headwall and said sidewall of said housing, respectively, said side portion of said cap member being in snug fitting abutment with said side wall of said housing, said head portion being disposed in spaced relation with respect to said sidewall to provide an insulating space therebetween, said cap member being rotatably attached to said stem member to allow rotation of said cap member with respect to said headwall of said housing, said cap member including a nipple means which is hollow and defines a nipple aperture therein, said nipple aperture being selectively alignable with said housing aperture in said headwall to allow fluid flow between said nipple means and said sterile chamber; and
   (d) sealing means positioned between said housing aperture in said headwall and said nipple aperture in said head portion to seal fluid flow therebetween when in alignment and to prevent fluid flow therebetween when not in alignment.

2. The syringe as defined in claim 1 wherein said sealing means comprises a rubber grommet peripherally positioned about the inner face between said housing aperture and said nipple aperture.

3. The syringe as defined in claim 2 wherein said rubber grommet is fixedly secured to said headwall to be rotatable therewith.

4. The syringe as defined in claim 2 wherein said rubber grommet is fixedly secured to said head portion of said cap member to be rotatable therewith.

5. The syringe as defined in claim 1 further comprising a tab means extending from said cap member and being movable with said cap member to be movable with respect to said sidewall of said housing between an opened and a closed position to indicate fluid flow through said housing aperture to be selectively allowed and prevented, respectively, said sidewall further including on the outer surface thereof an opened protrusion and a closed protrusion being selectively abutable against said tab means upon rotation of said cap member between the opened and closed positions, respectively.

6. The syringe as defined in claim 1 wherein said housing sidewalls are cylindrical.

7. The syringe as defined in claim 1 wherein said nipple means includes an attachment means to facilitate securement of a needle thereon.

8. The syringe as defined in claim 1 wherein said stem member is fixedly secured to said housing and rotatable with respect to said cap member to allow relative rotational movement therebetween.

9. The syringe as defined in claim 1 wherein said stem member is fixedly secured to said cap member and rotatable with respect to said housing to allow relative rotational movement therebetween.

10. A sealable syringe comprising:
    (a) a cylindrical housing defining a chamber therein which is sterile, said housing including a headwall, a cylindrical sidewall and an open end, said headwall defining a housing aperture therein and a stem member mounted extending axially outward therefrom;
    (b) a plunger located extending into said open end of said chamber and being axially movable with respect to said housing to vary the total volume of said chamber;
    (c) a cap member including a head portion and a cylindrical side portion located about said headwall and said sidewall of said housing respectively, said side portion of said cap member being in snug fitting abutment with said sidewall of said housing, said head portion being disposed in spaced relation with respect to said headwall to provide an insulating space therebetween, said cap member being rotatably attached to said stem member to allow rotation of said cap member with respect to said headwall of said housing, said cap member including a nipple means which is hollow and defines a nipple aperture therein, said nipple aperture being selectively alignable with said said housing aperture in said headwall to allow fluid flow between said nipple means and said sterile chamber;

(d) a rubber grommet fixedly secured to said headwall and positioned peripherally between said housing aperture in said headwall and said nipple aperture in said head portion to seal fluid flow therebetween when in alignment and to prevent fluid flow therebetween when not in alignment; and (e) tab means extending from said cap member and being movable with said cap member to be movable with respect to said sidewall of said housing between an opened and a closed position to indicate fluid flow through said housing aperture to be selectively allowed and prevented, respectively, said sidewall further including on the outer surface thereof an opened protrusion and a closed protrusion being upon rotation of said cap member between the opened position and the closed position, respectively.

* * * * *